US00PP35881P2

(12) United States Plant Patent
Ranney et al.

(10) Patent No.: US PP35,881 P2
(45) Date of Patent: Jun. 25, 2024

(54) ***LIGUSTRUM* PLANT NAMED 'NCLJ1'**

(50) Latin Name: *Ligustrum japonicum*
Varietal Denomination: NCLJ1

(71) Applicant: North Carolina State University, Raleigh, NC (US)

(72) Inventors: Thomas Green Ranney, Arden, NC (US); Andra Windorf Nus, Arden, NC (US); Irene Palmer, Arden, NC (US); Nathan P. Lynch, Arden, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 18/206,270

(22) Filed: Jun. 6, 2023

(51) Int. Cl.
*A01H 5/12* (2018.01)
*A01H 6/00* (2018.01)

(52) U.S. Cl.
USPC ..... Plt./226

(58) Field of Classification Search
USPC ..... Plt./226
CPC ..... A01H 5/12; A01H 5/00; A01H 6/00
See application file for complete search history.

(56) References Cited

PUBLICATIONS

Spring Meadow Kindly Japanese Privet, 2023 retrieved on Sep. 26, 2023 at https://springmeadownursery.com/plantfinder/kindly-54100, one page. (Year: 2023).*
Spring Meadow Nursery introduces 2023 Proven Winners Color Choice varieties, retrieved on Sep. 26, 2023 at https://springmeadownursery.com/about/press_releases/spring-meadow-nursery-introduces-2023-proven-winners-colorchoice-varieties, one page. (Year: 2023).*
Gilman et al. Ligustrum japonicum: Japanese Privet, UF IFAS Extension University of Florida, last modified Aug. 19, 2021, retrieved on Sep. 26, 2023 at https://edis.ifas.ufl.edu/publication/ST352, 9 pp. (Year: 2021).*

* cited by examiner

*Primary Examiner* — June Hwu
(74) *Attorney, Agent, or Firm* — Cassandra Bright

(57) ABSTRACT

A new and distinct cultivar of *Ligustrum* plant named 'NCLJ1' is disclosed, characterized rounded upright habit, white flowers, glossy evergreen foliage, and no apparent female fertility. The new variety is a *Ligustrum*, typically produced as an outdoor ornamental plant.

3 Drawing Sheets

Latin name of the genus and species: *Ligustrum japonicum.*

Variety denomination: 'NCLJ1'.

BACKGROUND OF THE INVENTION

The new cultivar is a product of a planned breeding program conducted by the inventors at a research nursery in Mills River, North Carolina. The objective of the breeding program was to produce new *Ligustrum* varieties with reduced fertility and invasiveness potential, as well as a favorable habit and attractive foliage. 'NCLJ1' was created by first developing a chemically-induced tetraploid plant derived from seed from open pollination of *Ligustrum japonicum* 'Davidson Hardy' (unpatented). This tetraploid seedling (H2000-024-029) was then hybridized (open pollination) with an unknown diploid *Ligustrum japonicum* resulting in a population of triploid cytotypes (H2011-134) in 2010. 'NCLJ1' was eventually selected from this triploid population based upon its combination of desirable traits. Triploid cytotypes were intentionally developed in an effort to reduce fertility, reseeding, and potential invasiveness.

The new variety was found and selected by the inventors in 2011 at the same research nursery in Mills River, North Carolina.

Asexual reproduction of the new cultivar 'NCLJ1' was first performed in July of 2013 in Mills River, North Carolina, by softwood cuttings treated with a basal dip of 5,000 ppm indole butyric acid (potassium salt) in water. Through subsequent propagation, multiple additional generations have been reproduced, having shown that the unique features of this cultivar are stable and reproduced true to type.

Date of first sale was Jun. 21, 2022, in Grand Haven, Michigan. This sale was made directly by the inventor or one who obtained the claimed invention directly or indirectly from the inventor. This sale and all public disclosures made between Jun. 21, 2022 and the filing of this application fall within the exception allowed under 102(b)(1).

SUMMARY OF THE INVENTION

The cultivar 'NCLJ1' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'NCLJ1.' These characteristics in combination distinguish 'NCLJ1' as a new and distinct *Ligustrum* cultivar:

1. Upright, rounded habit.
2. Dense branching.
3. Glossy evergreen foliage.
4. A triploid cytotype with no observed fruit production.

PARENT COMPARISON

Plants of the new cultivar *Ligustrum japonicum* 'NCLJ1' can be compared to the seed parent. Plants of 'NCLJ1' are similar to plants of the seed parent in most horticultural characteristics, however, plants of 'NCLJ1' differ in the following:

1. The new variety is a triploid cytotype, while the seed parent is a tetraploid cytotype.
2. The new variety is non-fruit bearing, while the seed parent is fruit bearing.

COMMERCIAL COMPARISON

Plants of the new cultivar *Ligustrum japonicum* 'NCLJ1' can be compared to the commercial variety *Ligustrum japonicum* 'Texanum', unpatented. Plants of 'NCLJ1' are similar to plants of 'Texanum' in most horticultural characteristics, however, plants of 'NCLJ1' differ in the following:

1. Growth habit of the new variety is more rounded, while the growth habit of this comparator is more upright.
2. The new variety is non-fruit bearing, while this comparator is fruit bearing.

BRIEF DESCRIPTION OF THE PHOTOGRAPHS

The photographs were taken using conventional techniques and although colors may appear different from actual colors due to light reflectance it is as accurate as possible by conventional photographic techniques.

DETAILED BOTANICAL DESCRIPTION

Figure 1:
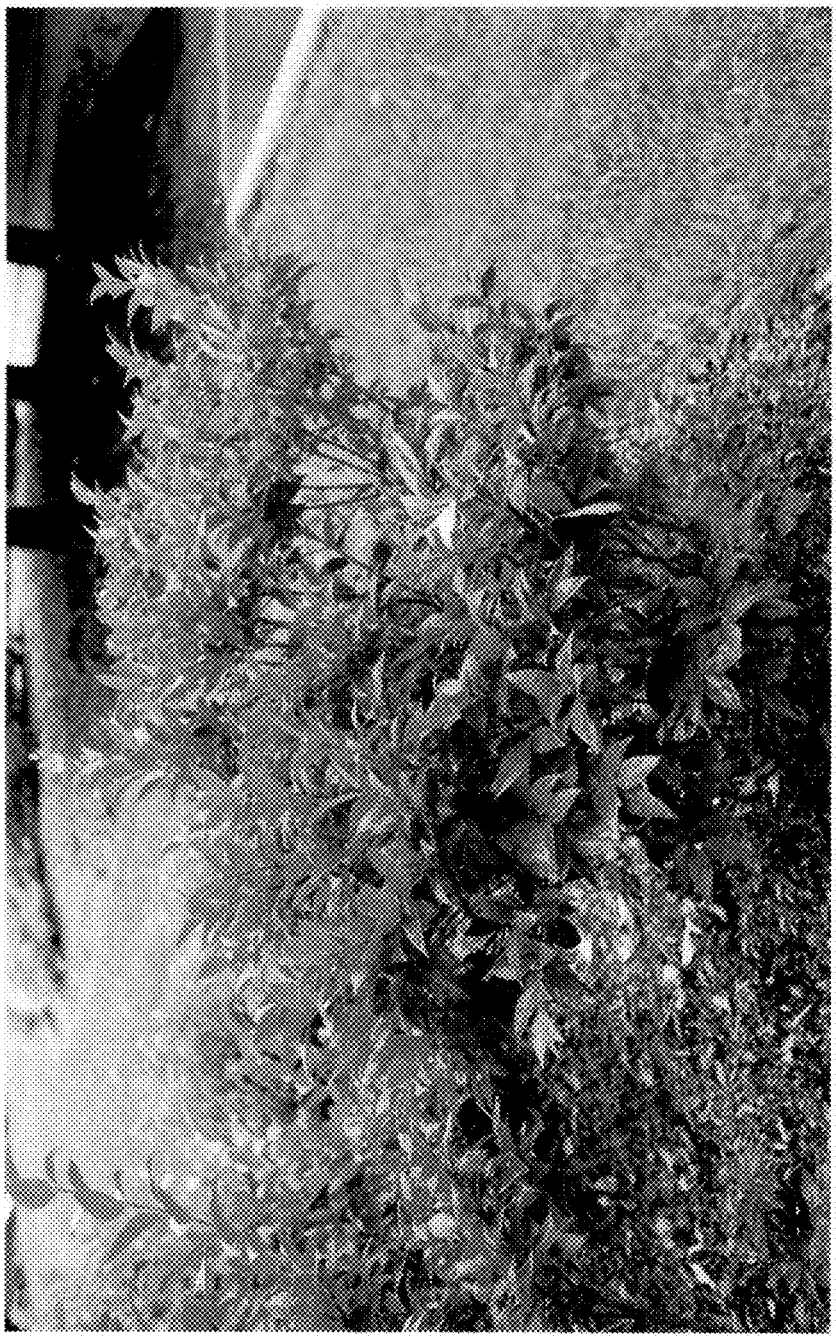
FIG. 1 is a photograph showing the form, foliage, and inflorescences of a five-year-old field-grown plant of 'NCLJ1' in May 2017, in Jackson Springs, North Carolina.
Figure 2:
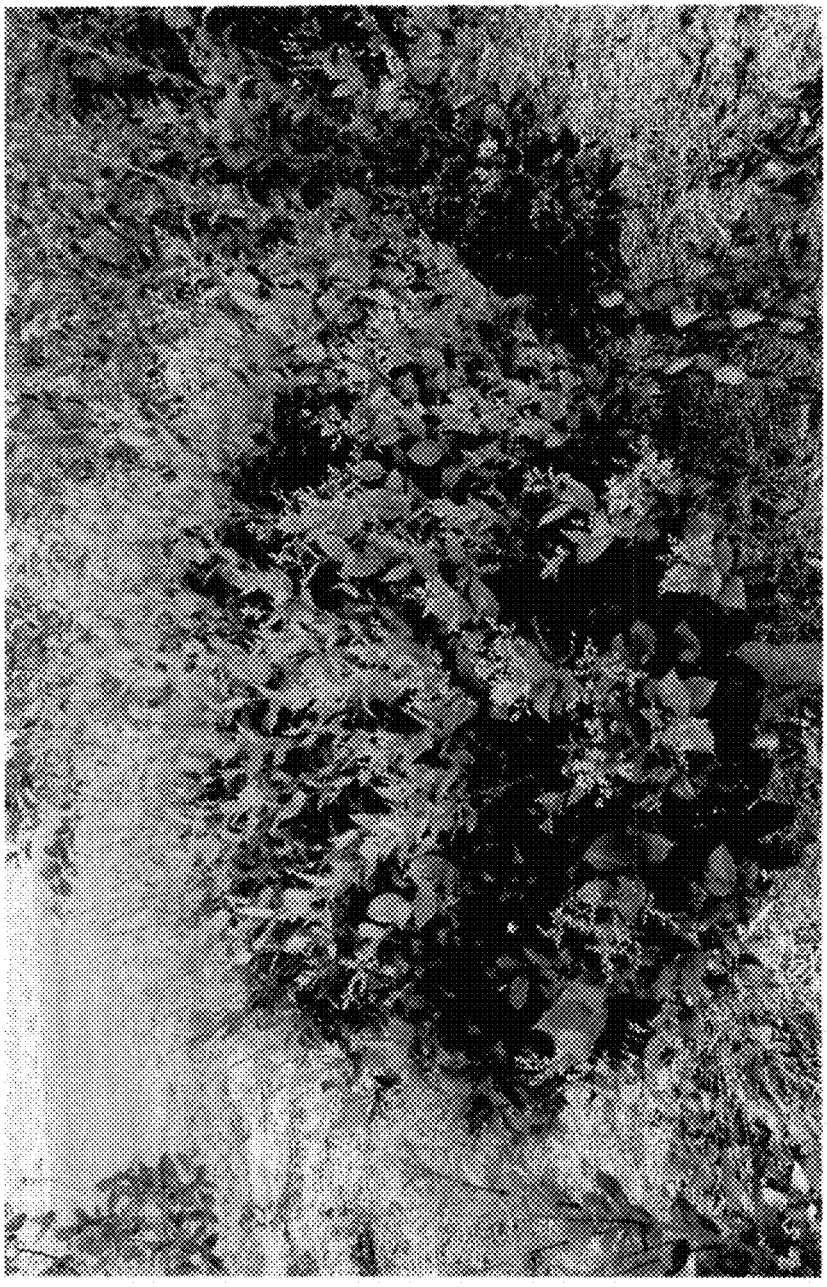
FIG. 2 is a photograph of a five-year-old field-grown plant of 'NCLJ1' plant with mature evergreen foliage and flower buds.
Figure 3:
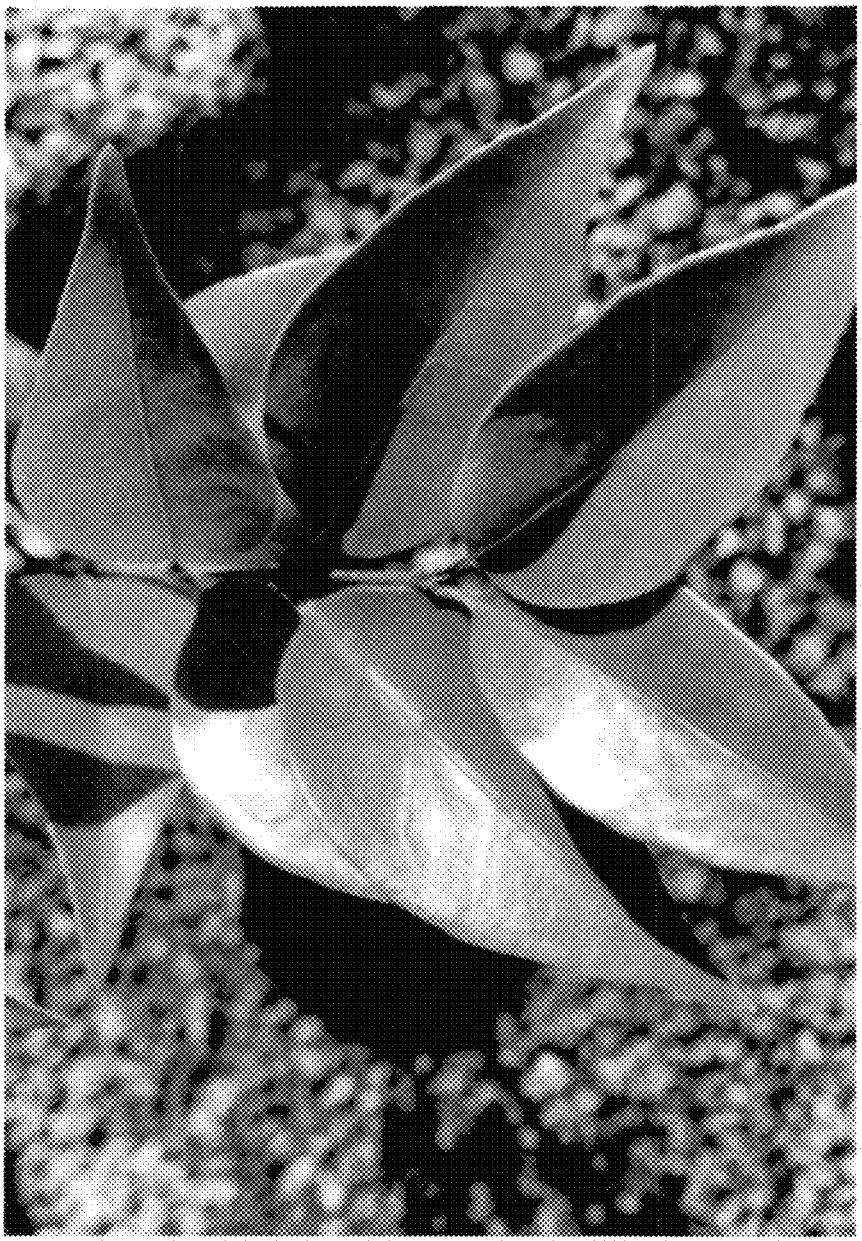
FIG. 3 is a photograph of the evergreen foliage of a four-year-old container-grown plant in summer of 2022, in Mills River, North Carolina.

In the following description, color references are made to The Royal Horticultural Society Colour Chart 2015, except where general terms of ordinary dictionary significance are used. The following observations and measurements describe 'NCLJ1' plants grown outdoors in Mills River, North Carolina. The plants were about 4 to 5 years old. Temperatures ranged from 5° C. to 10° C. at night to 18° C. to 27° C. during the day. No artificial light, photoperiodic treatments were given to the plants. Measurements and numerical values represent averages of typical plant types. Botanical classification: *Ligustrum japonicum* 'NCLJ1'.

PROPAGATION

Typical method: Softwood cuttings.
Root initiation: 3 to 5 days in the summer at 70° F.
Time to produce rooted cutting: 6 weeks in the summer at 70° F.
Roots: Moderately dense, low branching, medium thickness, and fleshy. Light tan to brown in color, not accurately measured with R.H.S. chart.

PLANT

Growth habit: Upright, dense, and rounded.
Height: 150 to 200 cm.
Plant spread: 100 to 150 cm.
Age of plant described: Approximately 5 years.
Shoots:
- *Current year's growth.*—Length: Average 16.5 cm. Diameter: About 0.15 cm. Color: RHS Yellow-Green 146A. Texture: Glabrous with lenticels about 0.2 cm long, colored RHS Brown 199D.
- *Prior year's growth.*—Length: Average 16.5 cm. Diameter: About 0.2 cm. Color: RHS Gray 197A. Texture: Glabrous with lenticels about 0.2 cm long, colored RHS Brown 199D.

Branches:
- *Woody branches* 2-4 *years old.*—Length: Average 23.7 cm. Diameter: Average 0.8 cm. Color: RHS Gray 197A. Texture: Glabrous with lenticels about 0.2 cm long, colored RHS Brown 199D.

Internode length: Average 2.6 cm.

FOLIAGE

Leaf:
- *Type.*—Simple.
- *Arrangement.*—Opposite.
- *Persistence.*—Evergreen.
- *Shape.*—Ovate.
- *Length.*—Average 6.6 cm.
- *Width.*—Average 3 cm.
- *Apex.*—Acute.
- *Base.*—Cuneate.
- *Margin.*—Entire.
- *Texture.*—Upper Side: Glabrous, glossy. Under Side: Glabrous, glossy.
- *Color.*—Emerging, Upper Side: RHS Yellow-Green 144A. Emerging, Under Side: RHS Yellow-Green 148C. Mature, Upper Side: RHS Green 137A. Mature, Under Side: RHS Yellow-Green 146C.
- *Venation.*—Type: Pinnate. Color, Mature Foliage: Upper side: RHS Yellow-Green 146C. Under side: RHS Yellow-Green 145A.

Petiole:
- *Shape.*—Rounded.
- *Length.*—Average 0.9 cm.
- *Diameter.*—About 0.15 cm.
- *Color.*—RHS Yellow-Green 145A.
- *Texture.*—Glabrous.

Dormant leaf bud:
- *Length.*—About 2 mm.
- *Diameter.*—About 1 mm.
- *Color.*—Near RHS Greyed-Green 197A.
- *Texture.*—Glabrous.

INFLORESCENCE

Natural flowering season: June in Mills River, North Carolina.
Inflorescence type: Terminal pyramidal panicles of small white flowers.
Quantity of flowers per inflorescence: About 120.
Inflorescence height: Average 11 cm.
Inflorescence diameter: Average 8.8 cm.
Fragrance: Light fragrance.
Lastingness of individual flowers: About 5 days.
Bud:
- *Height.*—About 0.3 cm.
- *Diameter.*—About 0.2 cm.

*Shape*.—Elliptical.
*Color*.—RHS White 155B.
*Texture*.—Glabrous.

Flower:
*Shape*.—Cruciform.
*Diameter*.—About 0.5 cm.
*Height*.—About 0.6 cm.

Petal:
*Quantity*.—4 per flower.
*Shape*.—Ovate, recurved.
*Length*.—About 0.4 cm.
*Width*.—About 0.2 cm.
*Apex*.—Acute.
*Base*.—Truncate.
*Margin*.—Entire.
*Texture*.—Glabrous.
*Color*.—RHS White NN155D.

Sepal:
*Length*.—About 0.3 cm.
*Width*.—About 0.2 cm.
*Apex*.—Rounded.
*Base*.—Fused.
*Margin*.—Fused.
*Texture*.—Glabrous.
*Color*.—RHS Yellow-White 158A.

Peduncle:
*Length*.—Average 3.3 cm.
*Diameter*.—About 0.1 cm.
*Texture*.—Finely pubescent.
*Color*.—RHS Yellow-Green 146A.

Pedicel:
*Length*.—Average 0.1 cm.
*Diameter*.—Less than 0.1 cm.
*Texture*.—Finely pubescent.
*Color*.—RHS Yellow-Green 146A.

REPRODUCTIVE ORGANS

Gynoecium:
*Pistil number*.—1.
*Pistil length*.—About 0.4 cm.
*Stigma color*.—RHS White NN155D.
*Style length*.—About 0.3 cm.
*Style color*.—RHS White NN155D.

Androecium:
*Stamen number*.—2.
*Anther shape*.—Oval.
*Anther size*.—About 0.2 cm.
*Anther color*.—RHS Yellow 2B.

OTHER CHARACTERISTICS

Fruit and seed: None observed.

Disease resistance: Neither resistance nor susceptibility to the normal diseases and pests of *Ligustrum* has been observed.

Drought tolerance and cold tolerance: At least USDA zone 7b; testing has not been completed in colder zones.

What is claimed is:

1. A new and distinct cultivar of *Ligustrum* plant named 'NCLJ1' as herein illustrated and described.

* * * * *